United States Patent [19]

Poloyko et al.

[11] Patent Number: 5,741,276
[45] Date of Patent: Apr. 21, 1998

[54] APPARATUS FOR FACILITATING THE PERFORMANCE OF SURGICAL PROCEDURES SUCH AS THE PLACEMENT OF SUTURES, LIGATURES AND THE LIKE

[75] Inventors: Alexandr Poloyko, Morton Grove; Raymond Firfer, Lincolnshire, both of Ill.

[73] Assignee: Innovative Surgical Instruments, Northbrook, Ill.

[21] Appl. No.: 623,154

[22] Filed: Jan. 28, 1996

[51] Int. Cl.[6] .................................................. A61B 7/04
[52] U.S. Cl. .......................... 606/144; 606/139; 112/169
[58] Field of Search .................................. 606/139, 144, 606/148, 145, 224, 147; 112/169, 80.03; 223/102, 104

[56] References Cited

U.S. PATENT DOCUMENTS

| | | | |
|---|---|---|---|
| 2,008,251 | 7/1935 | Hillbrand. | |
| 2,579,192 | 12/1951 | Kohl. | |
| 4,557,265 | 12/1985 | Adnersson | 128/340 |
| 4,935,027 | 6/1990 | Yoon | 606/146 |
| 4,957,498 | 9/1990 | Caspari et al. | 606/146 |
| 5,037,433 | 8/1991 | Wilk et al. | 606/139 |
| 5,059,201 | 10/1991 | Asnis | 606/144 |
| 5,100,418 | 3/1992 | Yoon et al. | 606/139 |
| 5,129,912 | 7/1992 | Noda et al. | 606/139 |
| 5,234,445 | 8/1993 | Walker et al. | 606/148 |
| 5,281,237 | 1/1994 | Gimpelson | 606/144 |
| 5,320,629 | 6/1994 | Noda et al. | 606/139 |
| 5,330,491 | 7/1994 | Walker et al. | 606/148 |
| 5,364,408 | 11/1994 | Gordon | 606/144 |
| 5,374,275 | 12/1994 | Bradley et al. | 606/144 |
| 5,382,257 | 1/1995 | Lewis et al. | 606/148 |
| 5,387,221 | 2/1995 | Bisgaard | 606/148 |
| 5,391,174 | 2/1995 | Weston | 606/148 |
| 5,395,382 | 3/1995 | DiGiovanni et al. | 606/148 |
| 5,403,328 | 4/1995 | Shallman | 606/144 |
| 5,417,699 | 5/1995 | Klein et al. | 606/144 |
| 5,433,722 | 7/1995 | Sharpe et al. | 606/148 |
| 5,439,467 | 8/1995 | Benderev et al. | 606/139 |
| 5,447,512 | 9/1995 | Wilson et al. | 606/139 |
| 5,458,609 | 10/1995 | Gordon et al. | 606/144 |
| 5,462,561 | 10/1995 | Voda | 606/144 |
| 5,466,241 | 11/1995 | Leroy et al. | 606/139 |
| 5,470,338 | 11/1995 | Whitfield | 606/144 |
| 5,472,446 | 12/1995 | de la Torre | 606/148 |
| 5,540,704 | 7/1996 | Gordon et al. | 606/144 |
| 5,571,119 | 11/1996 | Atala | 606/146 |
| 5,591,179 | 1/1997 | Edelstein | 606/144 |
| 5,601,557 | 2/1997 | Hayhurst | 606/72 |
| 5,601,572 | 2/1997 | Middleman et al. | 606/139 |

*Primary Examiner*—Michael Buiz
*Assistant Examiner*—Tina T. D. Pham
*Attorney, Agent, or Firm*—Dick and Harris

[57] ABSTRACT

An apparatus for facilitating the performance of surgical procedures such as the placement of sutures, ligatures and the like, having a cannula portion and a stylet portion. The apparatus is configured to hold a suturing needle or the like, having an attached thread. The apparatus holds the trailing end of the thread in an orientation internal to the apparatus for controlled handling and protection of the thread.

22 Claims, 3 Drawing Sheets

APPARATUS FOR FACILITATING THE PERFORMANCE OF SURGICAL PROCEDURES SUCH AS THE PLACEMENT OF SUTURES, LIGATURES AND THE LIKE

BACKGROUND OF THE INVENTION

1. The Field of the Invention

The present invention relates to the field of surgical apparatus, in particular, surgical apparatus for the facilitation of procedures such as the placement of sutures, ligatures and the like. The invention further relates to surgical apparatus such as may be used during laproscopic surgical procedures as well as open surgical procedures.

2. The Prior Art

Apparatus for facilitating the placement of sutures, ligatures, etc., during surgical operations are known. Such apparatus are often used, in order to extend the reach of the surgeon (or other personnel) within the body of the patient, without the surgeon having to have his/her hands in actual contact with the suturing needle or thread, and without the surgeon having to place his/her hands in close proximity to the site of the suture or ligature. Such apparatus facilitate the performance of surgical procedures under conditions where physical access to the operation site may be limited, either unintentionally, or intentionally, by anatomical alteration, as in the case of laproscopic surgical procedures.

Such prior art apparatus typically are configured to have a first, generally non-moving portion, which serves to provide a place for grasping by the surgeon and a holder or guide for the suturing needle, or ligature, as are often used in suturing and ligature procedures. A surgical thread is typically affixed to the end of the suturing needle.

The first portion of the apparatus typically will have a handle portion, a cannula portion comprising an elongated cannula or other structure sometimes having a longitudinally extending groove or slot therein, and a deployment head which may be configured to temporarily hold a suturing needle. A second portion of the apparatus is typically configured to be movably joined to or held within the first portion, and configured to be reciprocatingly movable relative to the first portion, so as to provide or impart a pushing force to the suturing needle, once the needle has been appropriately positioned in the deployment head. The pushing action serves to force the needle through the tissue of the patient. Where a ligature is being performed, instead of a suture, the pushing action serves to dislodge the ligature thread, from the deployment head.

Typically, the first and second portions of the apparatus are configured so as to be operably connected to one another, for generally one-handed operation. Another characteristic which is common to such prior art apparatus is that the thread attached to the suturing needle is not held or retained in any particular manner by any portion of the apparatus, but merely trails along the outside of the apparatus, and must either be held by hand by the surgeon, or temporarily wrapped in an informal manner, about a portion of the apparatus, to prevent the end of the thread from getting snagged, or simply becoming unsterile or contaminated by being brought into contact with other surfaces in an undesired uncontrolled manner.

In addition, in such prior art apparatus, once the suturing needle has been released by the apparatus, the suturing needle and thread are completely free of the apparatus such that the surgeon typically exerts no further control over the needle or thread by way of the apparatus, and instead must rely upon the use of forceps, and, due to space limitations, must remove the apparatus from the site of the operation, and replace it with a forceps in order to adequately handle the needle or thread.

In order to ligate a structure within the body cavity, the surgeon typically begins by using a flexible probe, instead of a sharp forceps, to form a passage around the structure to be ligated. In making the passage, typically by dissection, the surgeon must be particularly careful not to damage, tear, puncture or injure the surrounding tissue, as is particularly important given the close proximity of adjacent organs and tissues and especially when working around nerve bundles and other sensitive structures. Having made a passage, the surgeon, using a clamp, grasps the thread and passes the thread around the structure to be ligated. Using a second clamp, the surgeon grabs the free end of the ligature and draws the ligature through the passage and around the structure, having released the first clamp. In pulling the ligature, the surgeon must take care not to bind the ligature or tear it against the structure to be ligated. At this point, using clamps, a knot is tied and the ligation completed.

In performing such a procedure, in both open and laproscopic surgery, it is often necessary to work deep in the body cavity and, given the scissors action of clamps and other instruments typically used, the instrument may itself cause unintended damage as it is spread open and clamped closed. Moreover, it is often desirable to ligate a structure which is not perpendicular to the area of access, but rather, runs parallel to the opening. In such cases and, given the instruments used and tight surroundings, it is often difficult, if not impossible, to place a ligature without damage or extensive dissection. It would be desirable to provide a surgical apparatus for the facilitation of procedures such as the placement of sutures, ligatures and the like, which provides for a more controlled handling of the surgical thread, so that undesired contact between the thread and possibly non-sterile surfaces is precluded.

It also would be desirable to provide a surgical apparatus for the facilitation of procedures such as the placement of sutures, ligatures and the like, which provides for improved control of the surgical thread, for facilitation of the performance of the actual surgical procedure.

It would further be desirable to provide an apparatus for the deployment and handling of a suturing needle or ligature probe, in which the needle or probe can be partially or even completely deployed and thereafter retracted and repositioned within the patient, with the surgeon maintaining complete control over the needle or probe, if it is determined that the original positioning of the needle or probe needs to be changed.

It would still further be desirable to provide an apparatus for the deployment and handling of a suturing needle or ligature probe, which provides for a certain amount of control over the thread affixed to the needle or probe, even after deployment of the needle or probe, toward facilitating the completion of the suturing or ligature procedure.

It would still further be desirable to provide an apparatus for the facilitation of a surgical procedure which would be capable of deploying and pushing into place simply the knotted end of a surgical thread.

It is still further desirable to provide an apparatus for the facilitation of placing a ligature in a manner which minimized the risks of damaging the structure to be ligated and the surrounding tissue both when forming the passage to pass the ligature and when pulling the ligature into place.

It is still further desirable to provide an apparatus for the facilitation of placing a ligature in a vessel or structure which cannot be accessed perpendicularly.

These and other objects of the invention will become apparent in light of the present specification, including claims, and drawings.

SUMMARY OF THE INVENTION

The present invention comprises, in part, an apparatus for performing surgical procedures involved the placement and controlled manipulation of a thread, via a distal member, relative to tissues in a patient's body. The apparatus comprises a cannula member having a distal end and a proximate end. The cannula member includes means for releasably holding a first member, the means for releasably holding a first member, being operably disposed proximate the distal end of the cannula member. A stylet member has a distal end and a proximate end, and is further operably configured to be insertably received, at least along a portion of its length, by the cannula member. The stylet member further includes means for selectively ejecting a first member from the means for releasably holding a first member. Means are provided for facilitating handling of at least a portion of a thread affixed to the first member, during deployment of a first member, towards facilitating protection of the portion of the thread from undesired contact with potentially contaminated surfaces and for facilitating manipulation of the first member during one of the surgical procedures.

The cannula member comprises an elongated tube, having distal and proximate ends. The means for releasably holding a first member comprises a deployment head member, has a passage extending therethrough with at least first and second apertures disposed on an outer surface of the deployment member, wherein at least one of the at least first and second openings is operably configured to be aligned with and connected to one of the distal and proximate ends of the elongated tube of the cannula member. The passage through the deployment head is operably configured to receive, in its entirety, a suturing needle or spring wire or ligature. Alternatively, the passage through the deployment head member is operably configured to receive at least a portion of an elongated, substantially cylindrical probe member.

In a preferred embodiment of the invention, means are provided for facilitating grasping of the cannula member, operably disposed proximate to the proximate end of the cannula member. The means for facilitating grasping of the cannula member comprises at least one finger grip member operably connected proximate the other of the distal and proximate ends of the cannula member.

The stylet member comprises an elongated tube, having distal and proximate ends. The means for selectively ejecting a first member comprises an elongated substantially cylindrical flexible rod member.

In a preferred embodiment of the invention, means are provided for facilitating grasping of the stylet member operably disposed proximate the proximate end of the stylet member. The means for facilitating grasping of the stylet member comprises a thumb grip member operably connected proximate the proximate end of the stylet member.

The means for facilitating handling of at least a portion of a thread affixed to the first member comprise a passage extending through the flexible rod member with first and second openings disposed at first and second ends of the flexible rod member, wherein at least one of the at least first and proximate openings is operably configured to be aligned with and connected to one of the distal and proximate ends of the elongated tube of the stylet member, wherein the passage through the flexible rod member is operably configured to receive therethrough a surgical thread. In a preferred embodiment of the invention, the means for facilitating handling of at least a portion of a thread affixed to the first member further comprise a passage extending through at least a portion of a thumb grip member operably disposed proximate the proximate end of the elongated tube of the stylet portion, the passage being disposed in operable communication with the other of the distal and proximate ends of the elongated tube of the stylet member.

In a preferred embodiment of the invention, means for releasably engaging the cannula member and the stylet member, so that the cannula member and the stylet member are releasably precluded from movement relative to one another, are provided. The means for releasably engaging the cannula member and the stylet member further comprise a removable locking member, operably configured to selectively removably interconnect the cannula member and the stylet member.

In one embodiment of the invention, the first member is a needle. In an alternative embodiment of the invention, the first member is a probe for performing ligatures. In one embodiment of the invention, the probe is a flexible coil; in another, the probe is a knot positioned at a free end of the thread.

BEST MODE FOR CARRYING OUT THE INVENTION

While this invention is susceptible of embodiment in many different forms, there is shown in the drawings and will be described herein in detail, a specific embodiment with the understanding that the present disclosure is to be considered as an exemplification of the principles of the invention, and is not intended to limit the invention to the embodiments illustrated.

Figures 1, 10, 11, 12, 13, 14, 15, 16, 17:
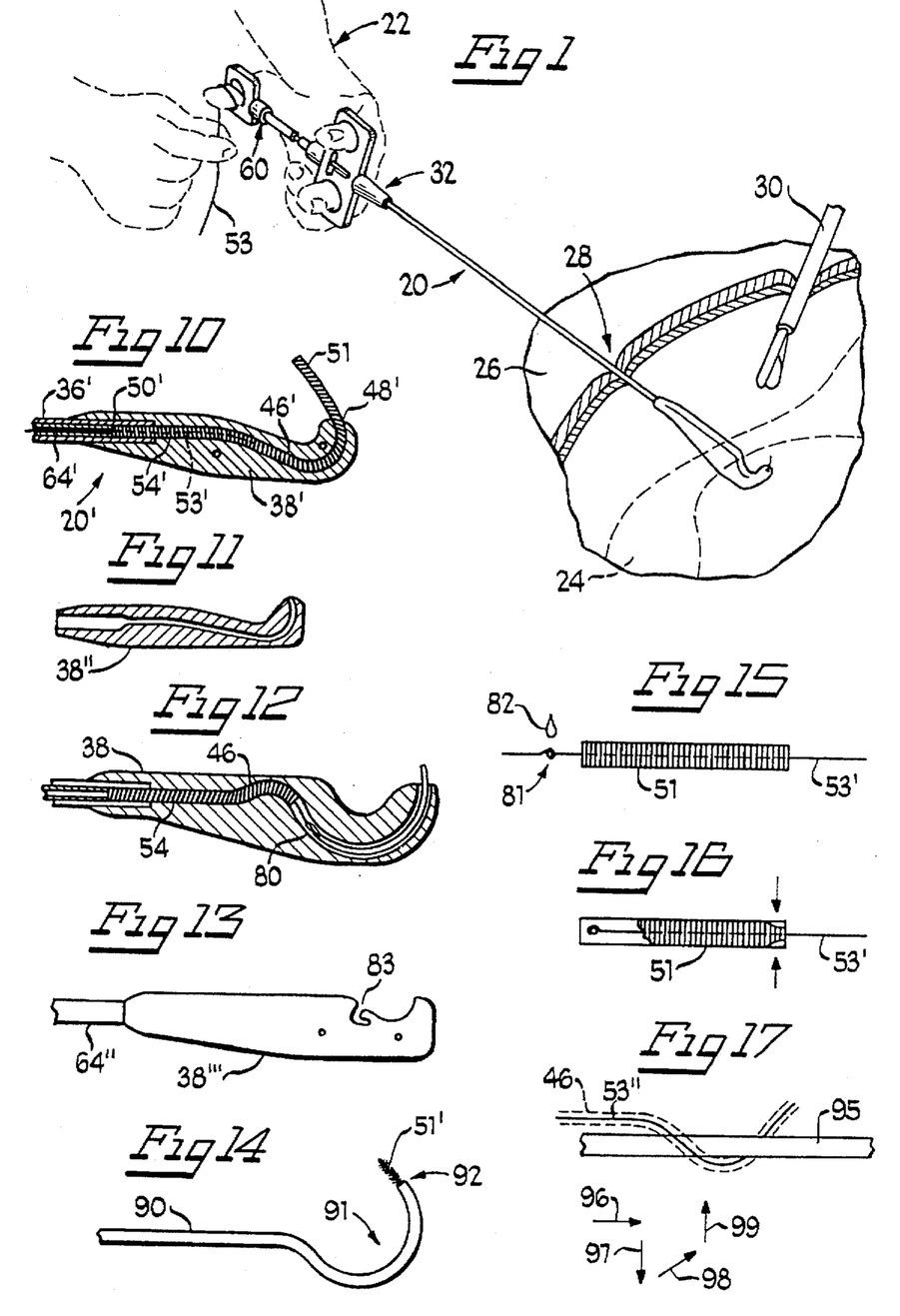
FIG. 1 is a perspective view of a surgical apparatus for performing suturing, ligatures, etc., according to a preferred embodiment of the invention, being used to perform a surgical procedure.
FIG. 10 is a side elevation, in section, of the deployment head of a surgical apparatus according to an alternative embodiment of the present invention, configured for performing ligature procedures.
FIG. 11 is a side elevation, in section, of a deployment head of a surgical apparatus according to still another alternative embodiment of the present invention.
FIG. 12 is a side elevation of the deployment head of the embodiment of FIGS. 1–8, wherein the ligature probe is in the form of a knotted segment of surgical thread.
FIG. 13 is a side elevation of a deployment head of a surgical apparatus according to still another alternative embodiment of the present invention.
FIG. 14 is a side elevation of the distal end of the cannula portion of a surgical apparatus according to still another alternative embodiment of the present invention configured for performing ligature procedures.
FIG. 15 is a side elevation of a flexible probe and thread portion of the stylet portion of the surgical apparatus according to FIG. 10, showing the assembly of the flexible rod and thread.
FIG. 16 is a side elevation of the flexible probe and thread portion of the stylet portion of the surgical apparatus according to FIG. 10, showing the flexible probe and thread in an assembled form.
FIG. 17 illustrates, somewhat schematically, the operation of an alternative embodiment of the present invention.

FIG. 1 illustrates a surgical apparatus 20, according to the present invention, being utilized during a surgical procedure. In particular, a laproscopic surgical procedure is being illustrated, in which apparatus 20 is being utilized by a surgeon 22 to place a suture in a structure 24 in a patient's body 26, through an aperture 28 in the body 26. A forceps or other clamping device 30 typically is also used in such a procedure.

Figures 5, 6, 6A, 7, 8, 9:
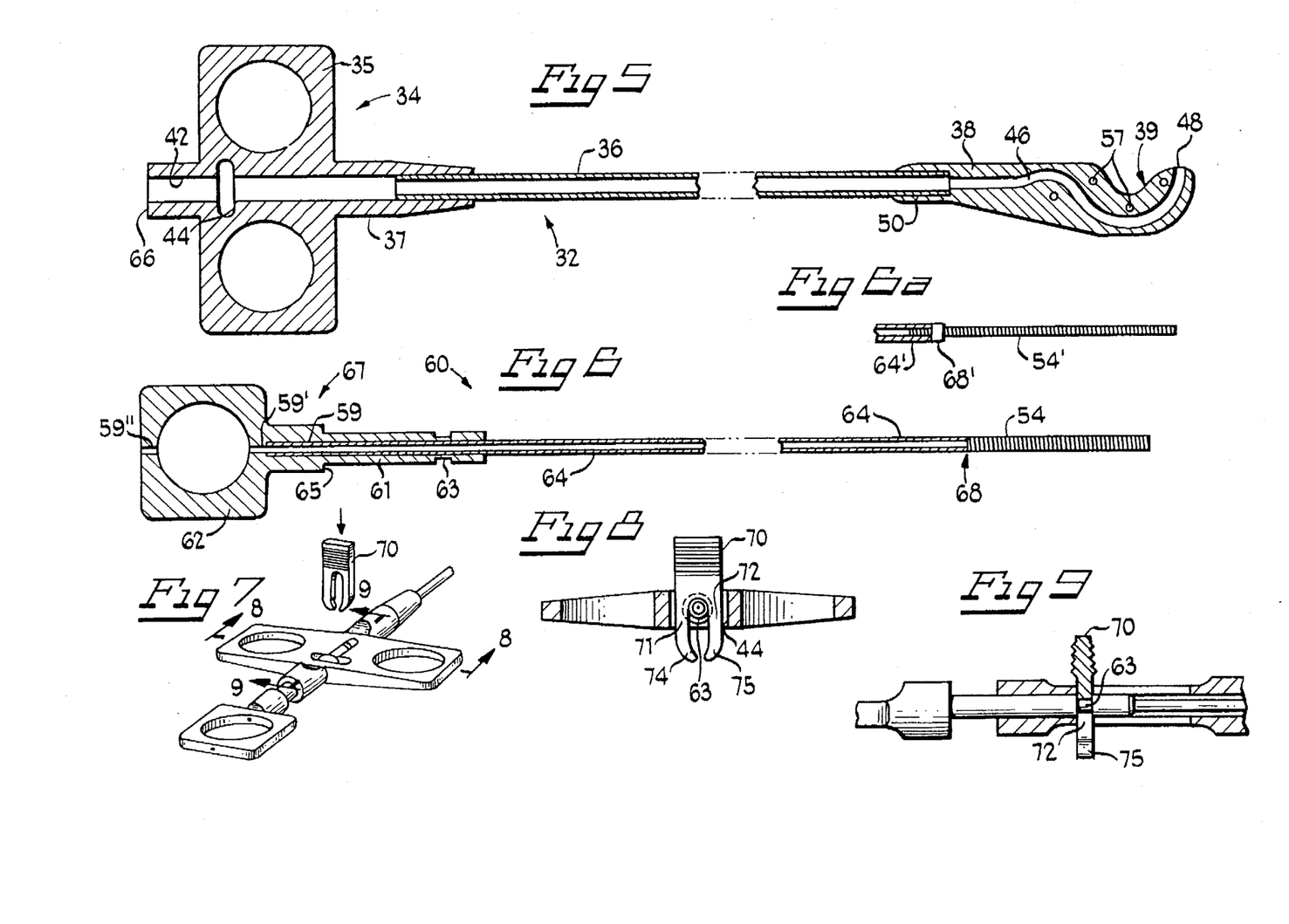
FIG. 5 is a side elevation, in section, of the cannula portion of the surgical apparatus according to FIG. 2.
FIG. 6 is a side elevation, in section, of the stylet portion of the surgical apparatus according to FIG. 2.
FIG. 7 is a perspective view of the handle end of the apparatus of FIGS. 1–6, illustrating a locking mechanism for the apparatus.
FIG. 8 is an elevation, in section, of the handle end of the apparatus of FIGS. 1–7, taken along line 8—8 of FIG. 7, and illustrating the operation of the locking mechanism.
FIG. 9 is an elevation, in section, of the handle end of the apparatus of FIGS. 1–8, taken along line 9—9 of FIG. 7, and illustrating the operation of the locking mechanism.

Apparatus 20 is shown in FIG. 2–6 wherein FIGS. 5 and 6 illustrate apparatus 20 in an unassembled state. As shown in FIGS. 2–6, apparatus 20 has a cannula portion 32, with an elongated tube 36, end section 34 adjacent the proximate end of elongated tube 36, and a deployment head 38, at the distal end of elongated tube 36. In a preferred embodiment of the invention, elongated tube 36 will be fabricated from biocompatable material which is capable of being fabricated or rendered hygienically sterile and suitable for use in surgical environments. Although great structural strength is not a requirement, the material of tube 36 should be sufficiently rigid and strong to withstand the stresses normally associated with surgical procedures such as laproscopic placement of sutures and the like. Accordingly, plastic, aluminum, stainless steel, graphite-based, or other known materials may also be used. End section 34 preferably will be provided with one or more finger grip members 35 emanating from opposite sides of a central, generally cylindrical section 37.

Figures 2, 4:
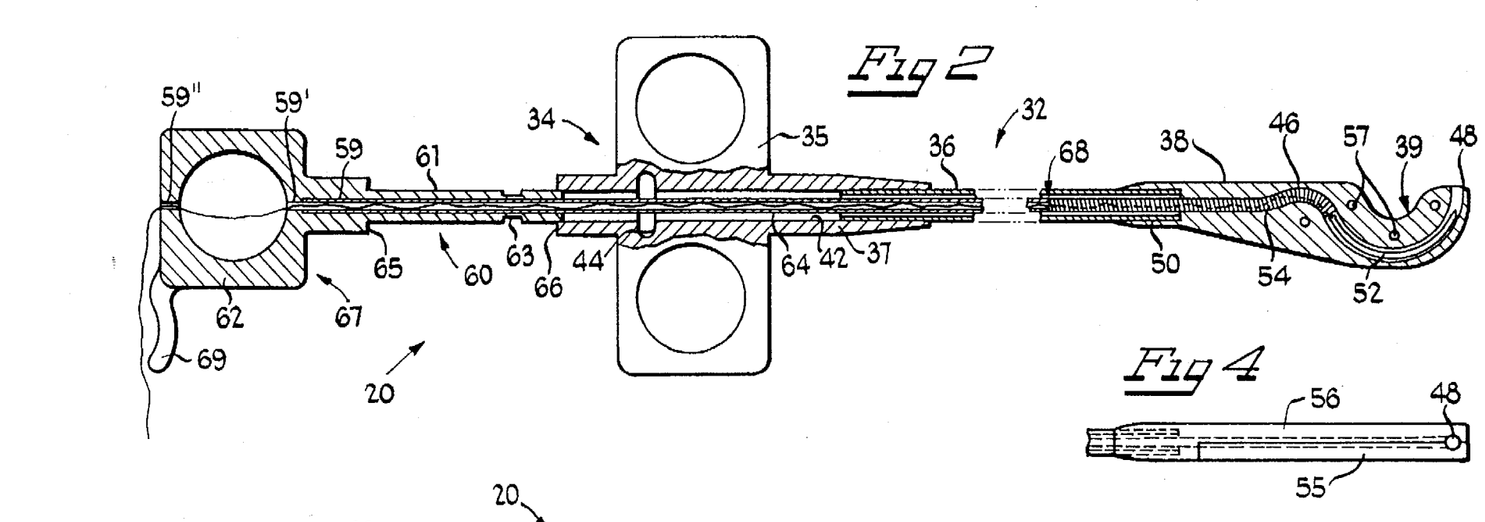
FIG. 2 is a side elevation, in section, of the surgical apparatus according to FIG. 1, showing a suturing needle and thread loaded in the apparatus, in an undeployed orientation.
FIG. 4 is a top plan view of the deployment head of the surgical apparatus of FIGS. 1–3, illustrating the aperture through which the suturing needle exits the apparatus.

End section 34 and/or deployment head 38, preferably may be fabricated, such as by injection molding, from plastic-based materials, and may be force-fitted onto tube 36, or otherwise substantially permanently attached.

It is contemplated that apparatus 20, generally, will be fabricated, as a whole, from materials which are sufficiently strong and sterilizable to satisfactorily perform the desired surgical procedures, but may also be sufficiently inexpensive so as to permit their use a single time, to be discarded in a safe manner thereafter.

End section portion 34 may be alternatively be provided instead merely with one or more forwardly curved projections, against which the surgeon's fingers can pull. Cylindrical section 37 has a longitudinally extending bore 42 which, for simplicity of manufacture, may have an internal diameter which is just slightly less than the outer diameter of tube 36, so that cylindrical section 37 can be forcibly fitted upon one, proximate, end of tube 36. In addition, a transversely extending slot 44 may be provided, the function of which is described with respect to FIGS. 7–9 hereinafter.

At the distal end of tube 36, opposite to end section 34, deployment head 38 is located. Deployment head 38 has a passage 46 extending through it, from exit aperture 48, and ending in countersunk hole 50. Passage 46 has an internal diameter which must be greater than the greatest diameter of needle 52, and of the greatest diameter of flexible rod 54 of stylet portion 60. Hole 50 preferably has an internal diameter which is slightly less than the outer diameter of tube 36, so that the end of tube 36 can be forcibly fitted into hole 50. Epoxy resin glue or the like can be used to affix tube 36 to head 38 (or to finger grip portion 34). In a preferred embodiment, head 38 is formed in two parts, 55, 56, which are more or less mating halves, although the portion of head 38 surrounding hole 50 preferably should all be formed as part of only one of the halves, as illustrated, part 56. By forming head 38 in two parts, head 38 can be manufactured by simple molding processes. Line 58 indicates the line of separation of parts 55, 56. Screws 57, fitting into suitably provided holes, can be used to hold parts 55 and 56 together. Head 38 may be provided with a cut-out region 39, which may be configured to accommodate or encircle a portion of a patient's anatomy, such as a vein, artery, etc., so that when needle 52 is deployed, as described with respect to FIG. 2, needle 52 can encircle the portion of anatomy without crowding or binding.

Stylet portion 60 includes tube member 64, end section 67 having thumb grip member 62 located at the proximate end of tube 64, and, at the distal end of tube 64, flexible rod 54, which may be configured as a tightly wound coil of spring steel or plastic. Thumb grip member 62 includes shaft 61, which has an external diameter which preferably is slightly less than bore 42 of finger grip portion 34 of cannula portion 32. In addition, shaft 61 may be provided with a reduced diameter section 63, which is positioned so as to align with slot 44, when stylet portion 60 has been thrust forward, relative to cannula portion 32, so as to preclude deployment of needle 52, as will be described further on in greater detail.

Tube 64 has an external diameter which is less than the internal diameter of tube 36, but is preferably greater than the diameter of passage 46. Flexible rod 54 is preferably fabricated as a tube formed from a tightly wound coil of spring steel or flexible plastic, and has an external diameter which is less than the diameter of passage 46. Flexible rod 54 will have a central passage which, while small, has sufficient diameter to permit the passage of surgical thread of a typical range of diameters. However, the passage in flexible rod 54 is smaller in diameter than the base of needle 52, so that needle 52 cannot become lodged in the central passage of flexible rod 54. Preferably, the external diameter of flexible rod 54 is slightly smaller than the internal diameter of tube 64, so that an end of flexible rod 54 can be insertingly received in a corresponding end of tube 64, and affixed there, such as by metal-bonding glue, by slight crimping of the end 68 of tube 64 or by use of an intermediate plastic fitting interposed between the end 68 of tube 64 and rod 54. FIG. 5a further illustrates flexible rod 54 configured for a smaller needle 52. While the internal diameter of tube 64 may be the same for various size needles the diameter of passage 46 is related to the size of needle 52 such that a smaller diameter needle necessitates a smaller diameter passage 46 and in turn a smaller diameter rod 54.

End section 67 further includes an internal bore 59, which extends along shaft 61 and has an internal diameter which preferably is slightly less than the external diameter of tube 64, so that tube 64 can be forcibly fitted into bore 59, and, if desired, affixed there by epoxy resin glue or the like. In addition, two smaller bores 59' and 59", which are aligned with bore 59, are also provided.

In a preferred embodiment of the invention, the total length of shaft 61, tube 64 and flexible rod 54 will be approximately equal to or slightly greater than the total length of bore 42, tube 36 and passage 46, minus the lengths of the portions of bore 42, tube 36 and passage 46 where they overlap. Accordingly, when stylet portion 60 is insertably received by cannula portion 32, and thrust forward relative to cannula portion 32, so that shoulder 65 of end section 67 abuts or nearly abuts shoulder 66 of end section 34, the extreme end of flexible rod 54 will arrive at or extend for a short distance beyond, exit aperture 48 of deployment head 38.

Preparation of apparatus 20 for use is as follows. Stylet portion 60 is inserted its full length into cannula portion 32, so that the extreme tip of flexible rod 54 is situated approximately at the end of tube 36. A fresh, sterile, unused suture needle 52, with attached thread 53 is obtained. Suture threads which are completely unused typically have a characteristic stiffness which permits them to be threaded, at least once, through narrow, elongated passages. Accordingly, thread 53 is threaded, starting at the extreme tip of flexible rod 54, backwards down through tube 64, until bore 59' is reached. Thread 53 will have sufficient length to be brought through bore 59" and beyond. Preferably, the total length of thread 53 will be one and one-half to two times or more the total length of apparatus 20, when stylet portion 60 is fully received within cannula portion 32, so that once thread 53 is passed through stylet portion 60, stylet portion 60 can be at least partially withdrawn from cannula portion 32, without thread 53 being drawn up into bore 59.

After thread 53 has been inserted into stylet portion 60, it is pulled through at its far end, until substantially all the slack is taken up. By grasping of the apparatus, in the manner generally shown in FIG. 1, and winding the thread end either about the thumb (as illustrated) or by winding the thread around or through thumb grip member 62, or around an advantageously provided projection 69 (FIGS. 2 & 3 only) or inserted into a groove or slot (not shown) thereon, and drawing back stylet portion 60 very slightly, relative to cannula portion 32, needle 52 is drawn into head 38. In order for this to be possible, at least a portion of passage 46 must have a sufficiently large diameter to accommodate needle 52. At least a portion of passage 46, leading to exit aperture 48, has a curvature which is substantially similar to the curvature of needle 52, so that needle 52 can be backed into passage 46 through aperture 48, and thereafter pushed out of passage 46, without binding. Different curvatures of passage 46 are contemplated to accommodate the different curvatures of different sized and shaped needles 52. Apparatus 20 is now ready for use.

Figure 3:
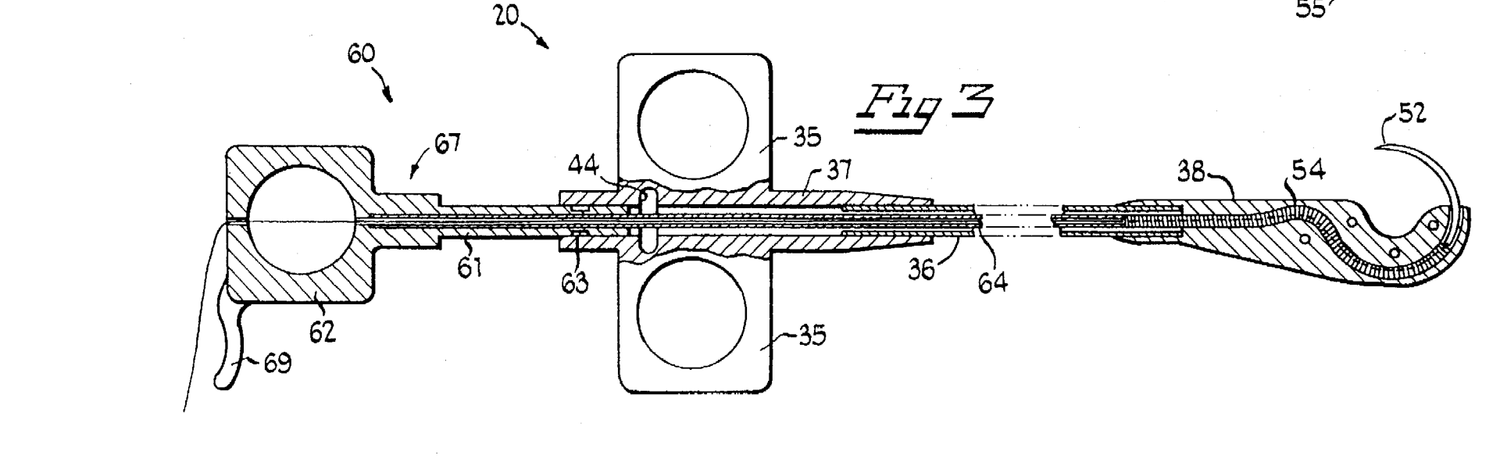
FIG. 3 is a side elevation, in section, of the surgical apparatus according to FIGS. 1 and 2, showing the suturing needle and thread in a partially deployed orientation.

In use, to begin a suturing procedure, a surgeon grasps the thumb grip member 62 and the finger grip members 35 with one hand. Stylet portion 60 is partially withdrawn from cannula portion 32, so that needle 52 is completely contained within head 38. The apparatus is then locked as later described. The excess length of thread 53 is wound about the thumb of the gripping hand. After the deployment head 38 as been positioned adjacent the tissue to be sutured and as desired by the surgeon, viewing a television monitor displaying an internal image of the field taken by an internal camera operated by operating room personnel as in the case of a laproscopic procedure, the surgeon deploys the needle by squeezing together the thumb grip member 62 and the finger grip members 35, in turn causing flexible rod 54 to push against the rear end of needle 52, prompting needle 52 to be moved out of passage 46, and into and possibly through the tissue to be sutured. Upon complete insertion of stylet portion 60 into cannula portion 32, needle 52 is completely ejected from head 38. During the procedure, the surgeon unwinds the excess thread from his/her thumb, as needed, after the needle has been satisfactorily positioned. Following ejection of needle 52, further manipulation of needle 52 and/or thread 53 can be accomplished by forceps 30, according to known surgical techniques.

The apparatus 20 of the present invention has several advantages over prior art apparatus. Apparatus 20 provides for a measure of control over the thread which is attached to the needle which is being positioned, in particular by having the thread run through the center and out of the end of the stylet portion 60. So long as the surgeon maintains control over the thread end, by wrapping about a thumb or a projection 69, or inserting the end in a groove or slit, the surgeon can partially eject the needle or probe, and then retract the needle, by pulling on the trailing end of the thread, if it is determined that the selected site for the suture or margin is not satisfactory. Depending somewhat upon the individual skill of the particular surgeon, even a completely deployed needle can be retracted back into head 38. Moreover as illustrated in FIG. 13, to facilitate the use of apparatus 20 a deployment head 38'" having disposed therein groove 83 may be provided to tie and place a knot. In practice the surgeon may manipulate apparatus 20 to grab the thread and retain it in groove 83 as the knot is formed and placed into position.

In order to facilitate the safe handling and use of apparatus 20, it may be desirable to lock needle 52 into a fully retracted position within head 38 so as to prevent needle sticks and the chance that needle 52 might unintentionally scrape, tear or otherwise injure tissue while apparatus 20 is being inserted into the patient and brought into position for use. To restrict deployment of the needle 52, a locking mechanism, illustrated in FIGS. 7–9, among others, is provided. As previously described, end section 34 has an slot 44, which extends transversely, completely through section 34. Shaft 61 of stylet portion 60 has a reduced diameter portion 63 which can be aligned with slot 44. The amount of insertion of stylet portion 60 into cannula portion 32, and corresponding degree of deployment of needle 52 is of course a function of the size of the particular needle 52. Accordingly, by changing from one particular apparatus 20 to another the longitudinal positions of either or both of slot 44 and reduced portion 63, relative to their respective end sections 34 and 67 locking can be effected for different size needles. In a preferred embodiment of the invention, when slot 44 and reduced portion 63 are aligned, needle 52 will be fully retracted within head 38, so that the surgeon can grossly manipulate apparatus 20, without having to specifically simultaneously grasp thumb grip member 62 and finger grip member 35.

In any configuration, once alignment has occurred, stylet portion 60 and cannula portion 32 can be held in their specifically aligned configuration, by the placement of locking member 70. In a preferred embodiment of the invention, locking member 70 is a clip member having two resilient arms 71, 72, which end in slightly curved hooks 74, 75, which curve inwardly toward one another. Hooks 74, 75 have rounded ends, and are separated by a space which is less than the diameter of reduced diameter portion 63. By pressing locking member 70 downwardly toward reduced diameter portion 63, in the direction of the arrow A in FIG. 7, hooks 74, 75 abut reduced diameter portion 63 and are forced apart. Once the ends of hooks 74, 75 have passed the widest part of portion 63, their resiliency causes hooks 74, 75 to move toward one another, further drawing locking member 70 into aperture 44, as shown in FIGS. 8 and 9. In order to remove locking member 70, reeded or knurled portion 76 is grasped, and locking member 70 is pulled away from apparatus 20 with sufficient force to overcome the spring force resistance of arms 71, 72, to spread arms 71, 72 apart until reduced diameter portion 44 is cleared.

As was previously mentioned, while the previously described preferred embodiment is configured for use in suturing procedures, the apparatus of the present invention, in an alternative preferred embodiment, can be utilized in ligature procedures, wherein a thread is tied around a portion of a patient's anatomy. In such an embodiment, the needle 52 may be omitted. Instead, a tightly coiled elongated probe structure, similar to that positioned at the end of stylet portion 60 of the previous embodiment, and having a surgical thread affixed to an end thereof, can be utilized. The probe is provided to give a "handle" to the thread to facilitate manipulation of the thread end around the structure around which the ligature is to be placed.

In this alternative embodiment, illustrated in FIG. 10, apart from the structure of the deployment head of the cannula portion, the rest of the structure of apparatus 20 is substantially identical, and has been generally omitted, having been previously described. Those portions of the embodiment of FIG. 10 which are substantially identical to those of the embodiment of FIGS. 1–9 are given like reference numerals, supplemented by a prime (').

In the embodiment of FIG. 10, probe 51, having a thread 53' attached to its end, is received within passage 46' of head 38'. Thread 53' is also insertingly received by flexible rod 54' and tube 64' of the stylet portion. Flexible rod 54' and tube 64' are, in turn, insertingly received by tube 36' of the cannula portion. Probe 51 will have an external diameter which is less than the internal diameter of passage 46', and will also have an external diameter which is substantially equal to the external diameter of flexible rod 54'. Since probe 51, being a metal coil, or plastic rod, is flexible, passage 46' may have various special curvatures, and, indeed, may by provided with several different types of curvature, as desired, as illustrated by FIG. 11, which shows alternative deployment heads 38". Once probe 51 has begun to exit head 38' at exit aperture 48', probe 51 will tend to have a generally straight configuration, for facilitating handling during the placement of the ligature following ejection of the probe 51 from head 38'.

In practice, the surgeon utilizing the alternative embodiment of the invention to ligate a structure would place head 38 of apparatus 20 into position proximate to the structure to be ligated. By squeezing together thumb grip member 62 and finger grip members 35 probe 51 is forced out of head 38 and either through or around the structure to be ligated. Using forceps as illustrated in FIG. 1 the surgeon grasps either the probe or the thread attached thereto to, in turn, form a knot and complete ligation. It can be seen that probe 51 serves to prevent the thread from binding against, tearing or otherwise damaging the structure to be ligated as the thread is manipulated by the surgeon since the thread is shielded by head 38.

In some particularly delicate forms of ligating, even the flexible structure of the flexible probe 51 is too robust and stiff and may cause tissue damage. In such procedures, instead of probe 51, a knot 80 (see FIG. 12) may be placed a short (one inch or less) distance from an end of a thread, and the resulting "tail" can be used as the "handle" for the thread end. The configuration of head 38 can be used for such procedures, or an alternative configuration (FIG. 14) could be used, in which, instead of the widened deployment head of the embodiments of FIGS. 1–10, in an alternative embodiment, no deployment head, as such, is used. Instead, merely an extension of the tube of the cannula portion 90 is provided, which may be narrowed or constricted at its extreme end 92 so as to stabilize the end of the thread until deployment and ejection of same by the flexible rod of the stylet portion.

The apparatus 20 of the present invention as illustrated in FIG. 14 has several advantages over prior art apparatus. Cannula portion 90 may be formed to have a variety of curved end portion 91 where the radius of the curve may permit placement of a ligature in various places. End portion 91 serves to both assist in forming a passage for placing the ligature thread and protect the structure to be ligated as well as the surrounding tissue and organs while the ligature is placed as the ligature thread is completely shielded within cannula portion 90 and specifically end portion 91.

One particular method for joining thread 53' to probe 51 is illustrated in FIG. 15. Specifically, thread 53' is drawn through the center passage of probe 51. A knot 81 is formed at the distal end of thread 53' and glue 82 is applied thereto in sufficient quantity to affix knot 81 within central passage of probe 51 and seal the passage closed. As illustrated in FIG. 16, thread 53' is drawn back through probe 51 until knot 81 is positioned within probe 51. The proximate end of probe 51 may then be crimped closed as illustrated by arrows B to further insure that thread 53' and probe 51 are satisfactorily joined.

While the various embodiments of deployment head 38 illustrated herein depict a passage 46 extending in a single plane from countersunk hole 50 to exit aperture 48, it is deemed within the scope of the present invention to modify deployment head 38 to permit a ligature to exit the end of deployment head 38 at a tangential or skewed direction. Having a ligature exit deployment head 38 at an angle may be accomplished by forming a non-linear passage 46 into deployment head 38. As schematically illustrated in FIG. 17 passage 46 may be formed to prompt a ligature to exit head 38 (not shown in FIG. 17) at such an angle, such as by following a helical path, so as to be able permit a surgeon to place a ligature 53" around a structure 95 running substantially parallel to the orientation of apparatus 20. As illustrated by arrows 96–99 ligature 53' may be prompted to move forward, down left and then up. Accordingly a ligature may be placed without having to force apparatus 20 into an orientation perpendicular to structure 95 thereby minimizing unnecessary damage and dissection of surrounding tissue.

The foregoing description and drawings merely explain and illustrate the invention and the invention is not limited thereto, except insofar as the appended claims are so limited as those skilled in the art who have the disclosure before them will be able to make modifications and variations therein without departing from the scope of the invention.

We claim:

1. An apparatus for performing surgical procedures involving the placement and controlled manipulation of a thread, via a distal member, relative to tissues in a patient's body, the apparatus comprising:

a cannula member having a distal end and a proximate end, the cannula member including means for releasably holding a first member, the means for releasably holding a first member, being connected to the distal end of the cannula member, a stylet member having a distal end and a proximate end, the cannula member and means for releasably holding a first member together forming an elongated, substantially rigid, substantially completely enclosed structure for facilitated placement and handling of first member, prior to deployment of same, the stylet member being operably configured to be insertably received, at least along a portion of its length, by the cannula member, the stylet member further including means for selectively ejecting a first member from the means for releasably holding a first member; and means for facilitating handling of at least a portion of a thread affixed to a first member, during deployment of a first member, towards facilitating protection of the portion of a thread from undesired contact with potentially contaminated surfaces external to the apparatus, the means for facilitating handling including a passage extending entirely through the stylet member, for insertably receiving therethrough a thread affixed to a first member, the cannula, the means for releasably holding a first member, and the stylet being operably configured so as to completely enclose a thread, being insertably received completely internally therethrough, during passage of the thread through the apparatus, until deployment of a first member, to which the thread is affixed, and further enabling the facilitated retraction of an ejected first member.

2. The apparatus according to claim 1, wherein the cannula member comprises an elongated tube, having distal and proximate ends.

3. The apparatus according to claim 2, wherein the means for selectively holding a first member comprises a deployment head member, having a passage extending therethrough with at least first and second apertures disposed on an outer surface of the deployment member, wherein at least one of the apertures is aligned with and connected to the distal end of the elongated tube of the cannula member.

4. The apparatus according to claim 3, wherein the passage through the deployment head member is operably configured to receive, in its entirety, a suturing needle.

5. The apparatus according to claim 3, wherein the passage through the deployment head is operably configured to receive at least a portion of an elongated, substantially cylindrical probe member.

6. The apparatus according to claim 1, further comprising means for facilitating grasping of the cannula member, operably disposed proximate the proximate end of the cannula member.

7. The apparatus according to claim 6, wherein the means for facilitating grasping of the cannula member comprises at least one finger grip member operably connected proximate the other of the distal and proximate ends of the cannula member.

8. The apparatus according to claim 3, wherein the stylet member comprises an elongated tube, having distal and proximate ends.

9. The apparatus according to claim 8, wherein the means for selectively ejecting a first member comprises an elongated substantially cylindrical flexible rod member.

10. The apparatus according to claim 1, further comprising means for facilitating grasping of the stylet member operably disposed proximate the proximate end of the stylet member.

11. The apparatus according to claim 10, wherein the means for facilitating grasping of the stylet member comprises a thumb grip member operably connected proximate the proximate end of the stylet member.

12. The apparatus according to claim 9, wherein the means for facilitating handling of at least a portion of a thread affixed to the first member comprises:

a passage extending through the flexible rod member with first and second openings disposed at first and second ends of the flexible rod member, wherein at least one of the at least first and second openings is operably aligned with and connected to the distal end of the elongated tube of the stylet member, wherein the passage through the flexible rod member is operably configured to receive therethrough a surgical thread.

13. The apparatus according to claim 12, wherein the means for facilitating handling of at least a portion of a thread affixed to the first member further comprises:

a passage extending through at least a portion of a thumb grip member operably disposed proximate the proximate end of the elongated tube of the stylet portion, the passage being disposed in operable communication with the other of the distal and proximate ends of the elongated tube of the stylet member.

14. The apparatus according to claim 1, further comprising means for releasably engaging the cannula member and the stylet member, so that the cannula member and the stylet member are releasably precluded from movement relative to one another.

15. The apparatus according to claim 14, wherein the means for releasably engaging the cannula member and the stylet member further comprises a removable locking member, operably configured to selectively removably interconnect the cannula member and the stylet member.

16. The apparatus according to claim 1, wherein the first member is a needle.

17. The apparatus according to claim 1, wherein the first member is a probe for performing ligatures.

18. The apparatus according to claim 17, wherein the probe is a flexible coil.

19. The apparatus according to claim 17, wherein the probe is a knot positioned at a free end of the thread.

20. The apparatus according to claim 2, wherein the means for releaseably holding a first member comprises a deployment region of the elongated tube of the cannula member, operably disposed proximate the distal end of the elongated tube, and having a substantially arcuate configuration.

21. The apparatus according to claim 3, wherein the cannula member has a longitudinal axis extending substantially parallel to the elongated tube thereof, and the passage through the deployment head member is operably configured such that the first member exits the deployment head member at a position which is laterally displaced from the longitudinal axis, and is prompted in a direction which is non-coplanar to the longitudinal axis.

22. An apparatus for performing surgical procedures involving the placement and controlled manipulation of a thread, via a distal member, relative to tissues in a patient's body, the apparatus comprising:

a cannula member having a distal end and a proximate end, the cannula member including means for releasably holding a first member, the means for releasably holding a first member, being connected to the distal end of the cannula member, a stylet member having a distal end and a proximate end, the stylet member being operably configured to be insertably received, at least along a portion of its length, by the cannula member, the stylet member further including means for selectively ejecting a first member from the means for releasably holding a first member; and means for facilitating handling of at least a portion of a thread affixed to the first member, during deployment of a first member, towards facilitating protection of the portion of the thread from undesired contact with potentially contaminated surfaces external to the apparatus, the cannula member being an elongated tube, having distal and proximate ends; the means for selectively holding a first member comprises a deployment head member, having a passage extending therethrough with at least first and second apertures disposed on an outer surface of the deployment member, wherein at least one of the apertures is aligned with and connected to the distal end of the elongated tube of the cannula member, and the deployment head member further having a notch disposed therein for facilitating manipulation of the thread, following deployment of the first member.

* * * * *

UNITED STATES PATENT AND TRADEMARK OFFICE
CERTIFICATE OF CORRECTION

PATENT NO. : 5,741,276
DATED : April 21, 1998
INVENTOR(S) : Alexandr Poloyko, et. al.

It is certified that error appears in the above-identified patent and that said Letters Patent is hereby corrected as shown below:

Title page, item [22] Filing Date should be--March 28, 1996--

Title page, item [75] Inventors: after "Firfer" add --M.D.--

Column 10, line 62, delete "We Claim:" and insert --CLAIMS.--

Signed and Sealed this

Eighth Day of February, 2000

Attest:

Q. TODD DICKINSON

Attesting Officer

Commissioner of Patents and Trademarks